(12) United States Patent
Behl et al.

(10) Patent No.: US 8,348,940 B2
(45) Date of Patent: Jan. 8, 2013

(54) METHODS AND SYSTEMS FOR FOCUSED BIPOLAR TISSUE ABLATION

(75) Inventors: Robert S. Behl, Palo Alto, CA (US); Morton Grosser, Menlo Park, CA (US); Alexander L. Huang, Menlo Park, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/538,795

(22) Filed: Jun. 29, 2012

(65) Prior Publication Data

US 2012/0271302 A1 Oct. 25, 2012

Related U.S. Application Data

(63) Continuation of application No. 13/239,071, filed on Sep. 21, 2011, now Pat. No. 8,216,231, which is a continuation of application No. 12/127,469, filed on May 27, 2008, now Pat. No. 8,043,289, which is a continuation of application No. 09/663,048, filed on Sep. 15, 2000, now Pat. No. 7,387,628.

(51) Int. Cl.
*A61B 18/14* (2006.01)

(52) U.S. Cl. .......................... 606/41; 606/50

(58) Field of Classification Search ............. 606/41, 606/50
See application file for complete search history.

(56) References Cited

U.S. PATENT DOCUMENTS

| | | | |
|---|---|---|---|
| 5,611,803 A | 3/1997 | Heaven et al. | |
| 5,672,173 A | 9/1997 | Gough et al. | |
| 5,672,174 A | 9/1997 | Gough et al. | |
| 5,724,988 A | 3/1998 | Dennehey et al. | |
| 5,766,134 A | 6/1998 | Lisak et al. | |
| 5,810,804 A | 9/1998 | Gough et al. | |
| 5,827,276 A | 10/1998 | LeVeen et al. | |
| 5,855,576 A | 1/1999 | LeVeen et al. | |
| 5,863,290 A | 1/1999 | Gough et al. | |
| 5,868,740 A | 2/1999 | LeVeen et al. | |
| 5,913,855 A | 6/1999 | Gough et al. | |
| 5,928,229 A | 7/1999 | Gough et al. | |
| 5,980,517 A | 11/1999 | Gough | |

(Continued)

FOREIGN PATENT DOCUMENTS

DE 2124684 11/1972

(Continued)

OTHER PUBLICATIONS

LeVeenTM Needle Electrode (brochure) Radio TherapeuticsTM Corporation, 2685 Marine Way, Mountain View, CA, 94043, 2 pages total.

(Continued)

*Primary Examiner* — Lee S Cohen

(74) *Attorney, Agent, or Firm* — Vista IP Law Group LLP

(57) ABSTRACT

Large tissue regions are treated using pairs of electrode arrays. The electrode arrays may be concave and disposed in tissue so that their concave portions are opposed to each other. Axial conductors may be provided extending from the arrays and toward each other in order to increase the heating of tissues lying along the axis between the deployed electrode arrays. By properly spacing the electrode arrays apart and selecting the diameters of the arrays, desired volumes of tissue may be treated, typically with a bipolar, radiofrequency current.

20 Claims, 13 Drawing Sheets

U.S. PATENT DOCUMENTS

| | | | |
|---|---|---|---|
| 6,022,354 | A | 2/2000 | Mercuri et al. |
| 6,071,280 | A | 6/2000 | Edwards et al. |
| 6,090,105 | A | 7/2000 | Zepeda et al. |
| 6,165,175 | A | 12/2000 | Wampler et al. |
| 6,179,832 | B1 | 1/2001 | Jones et al. |
| 6,312,429 | B1 | 11/2001 | Burbank et al. |
| 6,337,998 | B1 | 1/2002 | Behl et al. |
| 7,195,629 | B2 | 3/2007 | Behl et al. |
| 7,387,628 | B1 | 6/2008 | Behl et al. |
| 8,043,289 | B2 | 10/2011 | Behl et al. |
| 8,216,231 | B2 * | 7/2012 | Behl et al. ............ 606/41 |
| 2002/0022864 | A1 | 2/2002 | Mahvi et al. |
| 2002/0156472 | A1 | 10/2002 | Lee et al. |

FOREIGN PATENT DOCUMENTS

| | | |
|---|---|---|
| JP | 2000-500033 | 1/2000 |
| WO | WO98/25539 A1 | 6/1998 |
| WO | WO98/52480 A1 | 11/1998 |
| WO | WO99/25260 A1 | 5/1999 |
| WO | WO99/32041 A1 | 7/1999 |
| WO | WO00/06046 A1 | 2/2000 |

OTHER PUBLICATIONS

European Patent Office Search Report for EP Patent Application No. 01973032.4-2305, Applicant: Radiotherapeutics Corporation; Form EPO 1507.0 (03.95), dated Aug. 18, 2005 (5 pages).

Office Action dated Feb. 27, 2009 in Canadian Application No. 2,421,795, International Filing Date: Sep. 14, 2001, Applicant: Boston Scientific Limited, (3 pages).

PCT International Search Report for PCT/US01/28707, Applicant: Radiotherapeutics Corporation, Form PCT/ISA/210 and 220, dated Jan. 10, 2002, (6 pages).

PCT Written Opinion of the International Search Authority for PCT/US01/28707, Applicant: Radiotherapeutics Corporation, Form PCT/ISA/237, dated Dec. 23, 2002, (4 pages).

PCT International Preliminary Report on Patentability (Chapter I of the Patent Cooperation Treaty) for PCT/US01/28707, Applicant: Radiotherapeutics Corporation, Form PCT/IB/326 and 373, dated Jun. 24, 2003, (3 pages).

Office Action dated Feb. 22, 2011 in Japanese Application No. 2002-526288, Applicant: Boston Scientific Limited, including English Translation (7 pages).

* cited by examiner

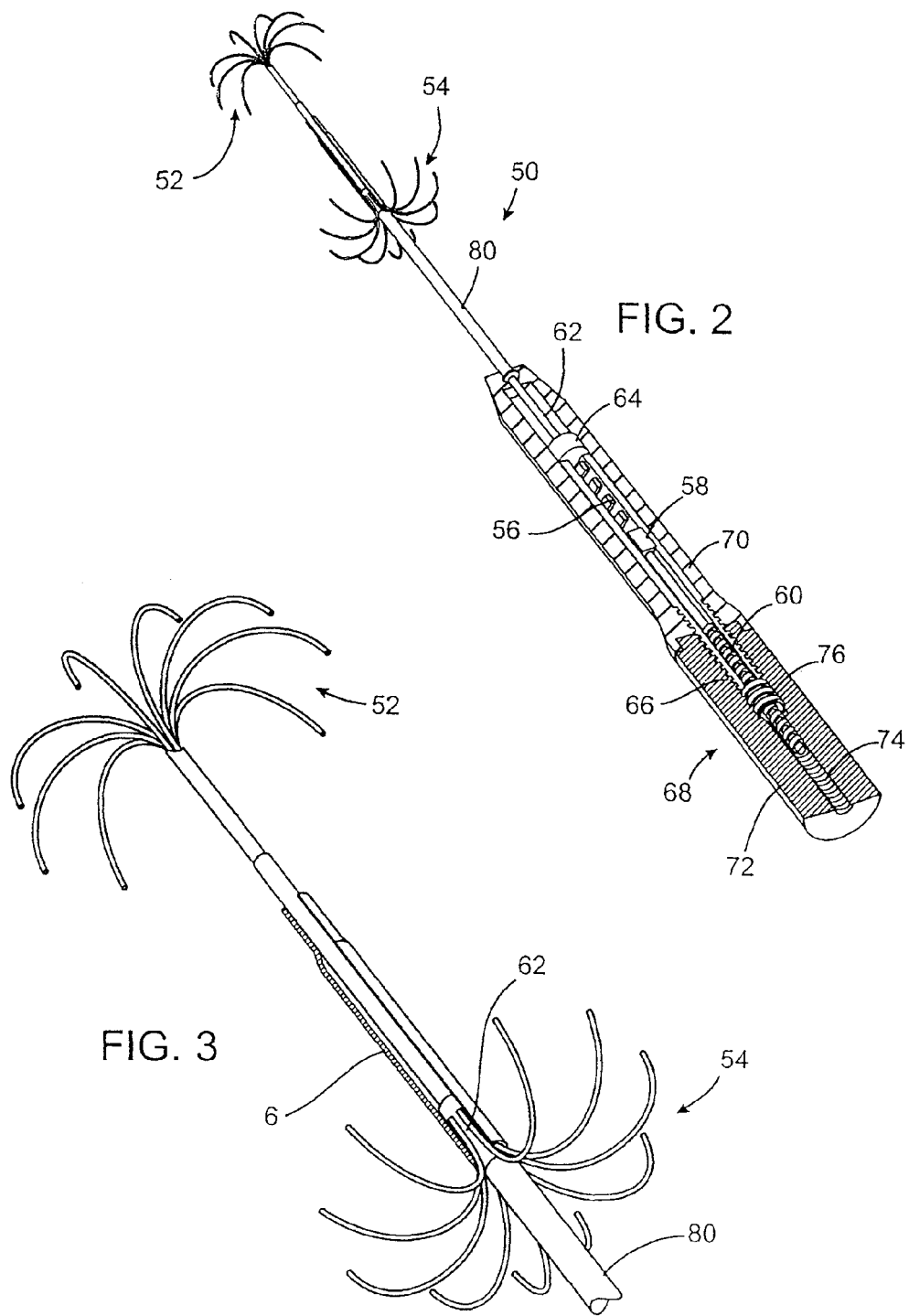

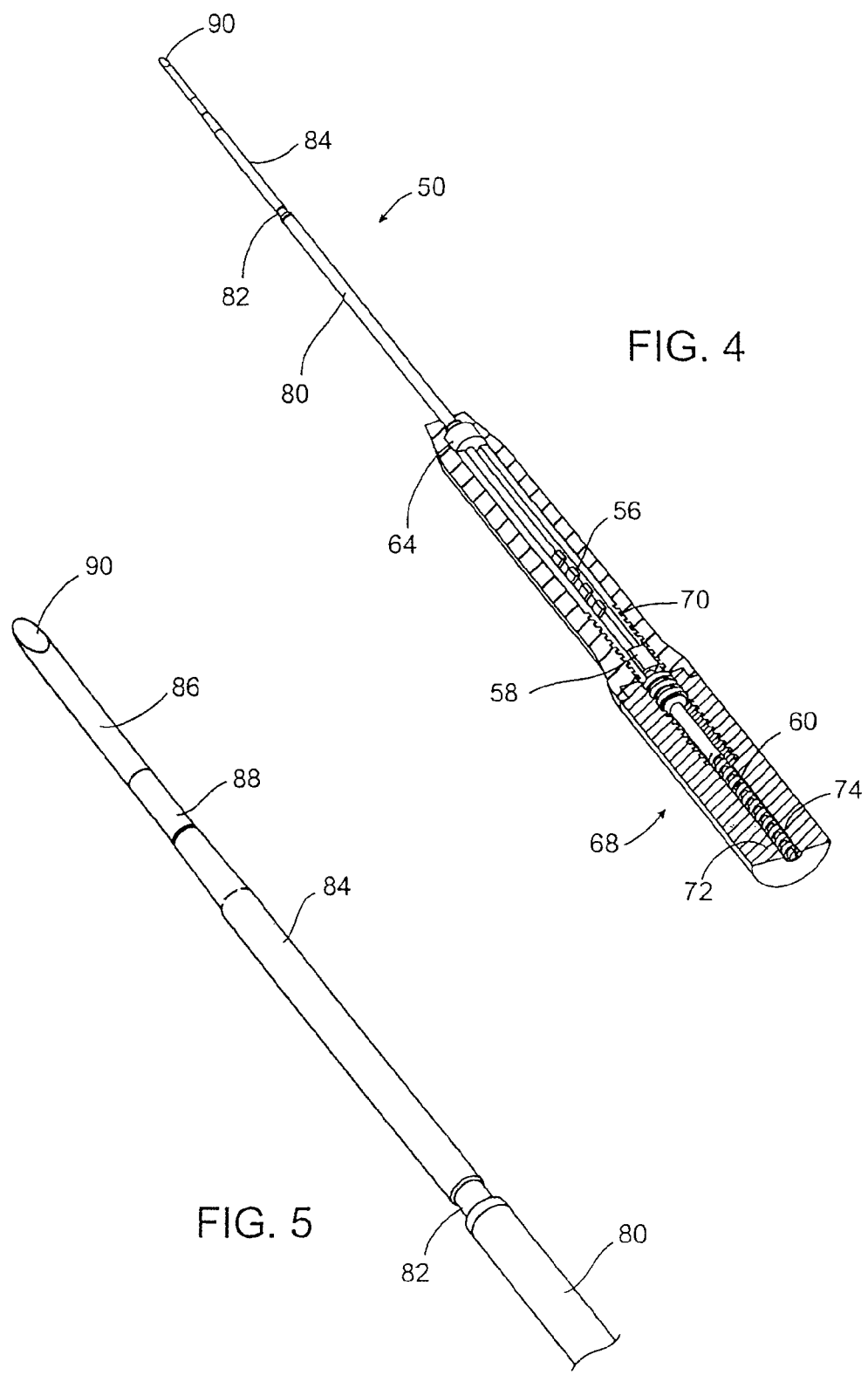

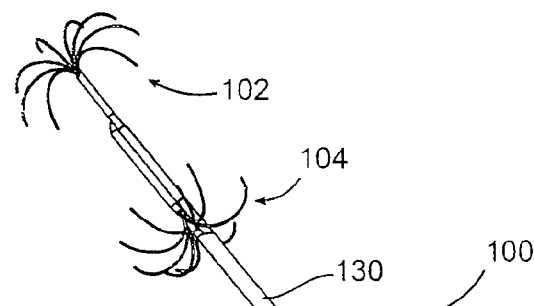
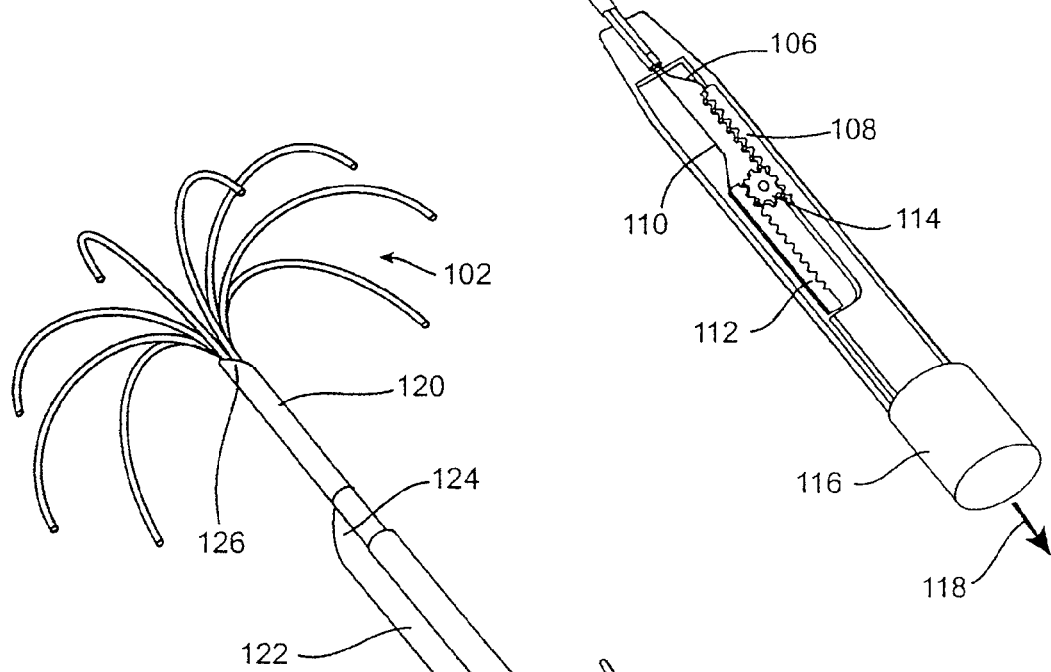
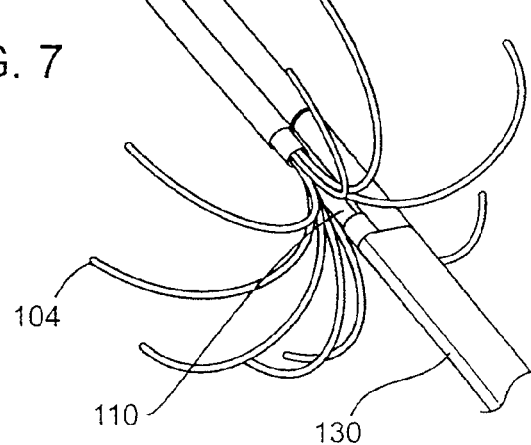
FIG. 6
FIG. 7

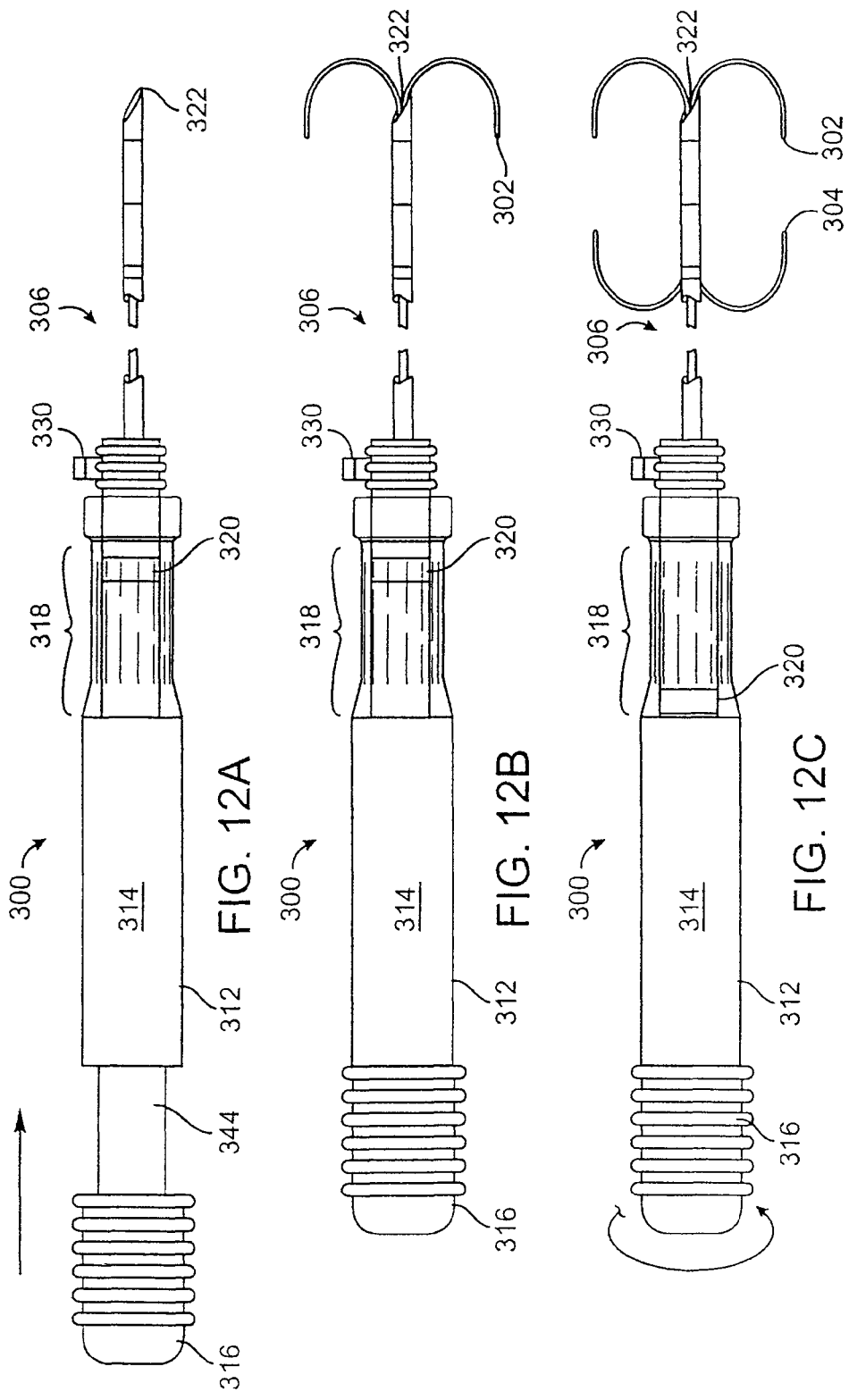

METHODS AND SYSTEMS FOR FOCUSED BIPOLAR TISSUE ABLATION

RELATED APPLICATION DATA

This application is a continuation of U.S. patent application Ser. No. 13/239,071, filed on Sep. 21, 2011, now U.S. Pat. No. 8,216,231, which is a continuation of U.S. patent application Ser. No. 12/127,469, filed on May 27, 2008, now U.S. Pat. No. 8,043,289, which is continuation of U.S. patent application Ser. No. 09/663,048, filed on Sep. 15, 2000, now U.S. Pat. No. 7,387,628, the entire disclosures of which are expressly incorporated by reference herein.

BACKGROUND OF THE INVENTION

1. Field of the Invention

The present invention relates generally to the structure and use of radiofrequency electrosurgical apparatus for the treatment of solid tissue. More particularly, the present invention relates to an electrosurgical system having pairs of electrode arrays which are deployed to treat large volumes of tissue, particularly for the treatment of tumors in the liver and other tissues and organs.

The delivery of radiofrequency energy to treatment regions within solid tissue is known for a variety of purposes. Of particular interest to the present invention, radiofrequency energy may be delivered to diseased regions in target tissue for the purpose of causing tissue necrosis. For example, the liver is a common depository for metastases of many primary cancers, such as cancers of the stomach, bowel, pancreas, kidney, and lung. Electrosurgical probes for deploying multiple electrodes have been designed for the treatment and necrosis of tumors in the liver and other solid tissues. See, for example, the LeVeen™. Needle Electrode available from RadioTherapeutics Corporation which is constructed generally in accord with published PCT application WO 98/52480.

The probes described in WO 98/52480 comprise a number of independent wire electrodes which are extended into tissue from the distal end of a cannula. The wire electrodes may then be energized in a monopolar or bipolar fashion to heat and necrose tissue within a defined generally spherical volumetric region of target tissue. In order to assure that the target tissue is adequately treated and to limit damage to adjacent healthy tissues, it is desirable that the array formed by the wire electrodes within the tissue be precisely and uniformly defined.

Despite the significant success that has accompanied use of the LeVeen™. Needle Electrode in treating solid tissue tumors, the ability to treat particular types of tumors has been somewhat limited. For example, the ability to produce very large tissue lesions, for example lesions having volumes greater than 30-35 cm$^3$, has been problematic. In addition, such larger tumors tend to be less spheroidal in shape than smaller tumors. Since the LeVeen™. Needle Electrode produces generally spheroidal lesions, the ability to treat larger, non-spheroidal tumors can be limited. Additionally, the ability to treat highly vascularized tissues and/or tissue near a large blood vessel has also been limited. In the latter cases, heat being introduced by the electrode can be rapidly carried away by circulating blood, making uniform heating and control of temperature in the vascularized tissues difficult. Uniform heating and temperature control of the tissue being treated is, of course, one prerequisite to obtaining homogenous lesions in and around the tumors.

The ability to provide uniform heating and the creation of homogenous tissue lesions is particularly difficult with bipolar devices. The two bipolar electrodes may be placed in regions with quite different perfusion characteristics, and the heating around each pole can be quite different. That is, one pole may be located adjacent to a large blood vessel, while the other pole may be located adjacent to tissue which is less perfused. Thus, the pole located in the less perfused tissue will heat the tissue immediately surrounding the electrode much more rapidly than the tissue surrounding the opposite polar electrode is heated. In such circumstances, the tissue surrounding one pole may be preferentially heated and necrosed, while the tissue surrounding the other pole will neither be heated nor necrosed sufficiently.

For all these reasons, it would be desirable to provide improved electrosurgical methods and systems for treating tumors in the liver and other body organs. It would be particularly desirable if the methods and systems could produce relatively large lesions (regions of necrosed tissue) within the solid tissue, preferably being capable of producing lesions having volumes greater than 30-35 cm$^3$, more preferably greater than 70 cm$^3$, and even more preferably greater than 150 cm$^3$, or larger. In addition, it would be desirable to provide methods and systems which can uniformly produce tissue lesions in highly vascularized tissues, such as the liver, and even more particularly in tissues which are unevenly perfused, such as tissues which are near major blood vessels, in such organs. It would be still further desirable to provide methods and systems which can produce tissue lesions having a variety of geometries, such as ovoid and cylindrical, rather than just spheroidal. At least some of these objectives will be met by the invention of the present application.

2. Description of the Background Art

U.S. Pat. Nos. 5,827,276; 5,855,576; and 5,868,740 to LeVeen and German Patent Publication No. 2124684 to Stadelmayr describe devices for deploying pairs of axially spaced-apart electrode arrays. U.S. Pat. Nos. 6,090,105; 6,071,280; 5,928,229; 5,913,855; 5,863,290; 5,672,174; and 5,672,173, describe multiple electrode devices having coaxial electrode structures including a primary antenna and at least one curved secondary antenna that deploys from the primary antenna. See, also U.S. Pat. No. 5,611,803 and WO 99/32041.

SUMMARY OF THE INVENTION

The present invention provides improved methods, apparatus, and kits for performing electrosurgical treatment of tissues and in particular for performing radiofrequency tissue necrosis for the treatment of tumors and diseased tissues. The methods, apparatus, and kits are particularly useful for creating large volume tissue lesions, such as those having volumes above 30 cm$^3$, often above 70 cm$^3$, and sometimes above 150 cm$^3$, or larger. In addition to being able to form relatively large volume tissue lesions, the methods, apparatus, and kits of the present invention are capable of producing highly uniform lesions where tissue necrosis is induced substantially uniformly through the entire treated region. Moreover, the present invention produces lesions having well-defined peripheries, typically ovoid or cylindrical, so that targeted tissue having different (non-spherical) geometries) may be necrosed with only minimum damage to adjacent healthy tissues.

In a first aspect of the present invention, probes for deploying electrode arrays comprise a shaft having a distal end and proximal end. A first array of electrodes is mounted on the shaft and is constructed or adapted to shift between a retracted configuration, typically within the shaft, and deployed configuration. The deployed configuration of the first electrode array will have a concave face, typically comprising a plurality of curved electrodes, more typically comprising at least three curved electrodes which evert when deployed from the shaft so that the electrodes each extend generally axially from the shaft, turn radially outward, and preferably turn around so that the tips of the electrodes are turned backwardly relative to their initial direction. In the most preferred embodiments, the electrode array will turn substantially completely, i.e., at or close to 180.degree., from the initial axial direction. The probe further includes a second electrode array having electrodes mounted on the shaft at a location spaced-apart proximally from the first array of electrodes. The electrodes of the second array are also capable of shifting between a retracted configuration and a deployed, where the deployed array typically comprises a plurality of everting electrodes, generally as described above. The first and second arrays, when deployed, are arranged so that the concave faces are opposed to each other on opposite sides of a treatment region.

In various preferred embodiments of the apparatus of the present invention, the probe may further include a self-penetrating tip, usually at the distal end of the shaft. The self-penetrating tip can take any conventional form, such as a sharpened tip, an electrosurgical tip (one adapted to penetrate tissue when connected to an electrosurgical power supply operating in a cutting mode), and the like. Alternatively, the probes may be introduced through or by exchange with a conventional cannula and stylet assembly as described generally in U.S. Pat. No. 5,827,276, the full disclosure of which is incorporated herein by reference.

The first and second electrode arrays will be mechanically coupled to the shaft to permit their deployment relative to the shaft. Usually, one electrode array will be mounted to extend in a distal direction and to evert from the shaft while the second array will be mounted to advance in a proximal direction relative to the shaft and to evert therefrom. Usually, the individual electrodes of each electrode array will be received within one or more cavities or lumens within the shaft so that the electrodes may be fully retracted into the shaft for introduction of the probe into tissue and removal of the probe from tissue. Operation of the two arrays may be coupled so that said arrays deploy simultaneously. More usually, however, the arrays will be separately deployable.

The first and second electrode arrays will each be connected or coupled to deployment mechanism(s) for advancing the electrodes relative to the shaft to achieve the desired everted deployment. Usually, the deployment mechanisms will comprise a first rod connected to the first electrode array and slidably disposed in or on the shaft and a second rod or tube connected to the second electrode array and slidably disposed in or on the shaft. In this way, distal advancement of the first rod or tube relative to the shaft causes the first electrode array to extend distally and evert radially outwardly relative to the shaft. Likewise, proximal retraction of the second rod relative to the shaft causes the second electrode array to draw proximally and evert radially outwardly from the shaft. Operation of the first and second rods or tubes may be coupled so that the user need perform only one deployment action using the probe. Usually, however, actuation of the two rods will not be coupled so that deployment of the two electrode arrays may be effected entirely separately. In particular embodiments, the first rod may be mounted coaxially within a central lumen or passage of a second tube to provide for a more compact design.

In a first exemplary embodiment, the first and second rods are mounted coaxially and threaded drive pins are mounted in a handle assembly in order to effect simultaneous advancement and retraction of the first and second rods. In a second exemplary embodiment, the first and second rods are mounted in parallel and a rack and pinion assembly is provided in a handle to effect simultaneous advancement and retraction of the rods. In a third exemplary embodiment, the distal and proximal arrays may be separately advanced, with one array being initially deployed and the second array being separately deployed, usually after the first array is satisfactorily located. Optionally, the electrode deployment device embodiments which permit separate array deployment could be used with only a single array, usually but not necessarily the distal array. While the distal array will normally be deployed first, there is no reason why the proximal array could not be deployed first, with or without subsequent deployment of the distal array. When only one array is deployed, the device could be used in a monopolar fashion with the deployed array being coupled to one pole of the power supply and a second, dispersive electrode (typically placed on an exterior body surface) being coupled to the other pole of the power supply. In the illustration of the third embodiment, the distal array is deployed by advancing a rod which extends axially through the length of the device, typically by depressing a knob at the proximal end of the device. The proximal array, in contrast, is separately deployed by rotating a threaded sleeve in the device, typically using the same knob which is used to advance the distal array. Optionally, a marker is provided on the handle so that the deployment of the proximal and/or distal array can be visually determined.

The first and second electrode arrays will typically comprise a plurality of single electrode elements, usually including at least three electrode elements, frequently including five or more electrode elements, and often including ten or more electrode elements. Electrode elements will usually be configured to diverge and in come cases evert from the shaft in a simple curve having a generally constant radius as the electrode advances. Usually, the distal tips of each electrode will be circumferentially spaced-apart by equal distances, although some variation in spacing may be acceptable. The construction and configuration of the electrode elements is described in detail in U.S. Pat. No. 6,050,992, the full disclosure of which is incorporated herein by reference.

Once deployed, the electrode arrays will span a planar area which is disposed generally transverse to the axis of the shaft. The planar area which is spanned will be generally circular, typically having an area in the range from 3 cm$^2$ to 20 cm$^2$ (when the electrodes are fully deployed), often in the range from 3 cm$^2$ to 15 cm$^2$, and preferably in the range from 6 cm$^2$ to 13 cm$^2$. The areas of the first and second electrode arrays will usually be approximately equal, though that is not necessarily the case at all times. In some instances, it may be desirable to use electrode arrays having differing diameters and planar areas in order to produce lesions having different geometries. It will be appreciated that spaced-apart, axially aligned electrode arrays having circular peripheries with identical diameters will produce generally cylindrical lesions, while arrays having different diameters will produce lesions having conical sections.

Preferably, the first and second electrode arrays will be spaced-apart along an axial line therebetween, usually through the shaft. Preferably, the arrays are spaced-apart by distance in the range from 2 cm to 10 cm, usually from 3 cm to 7 cm, and preferably from 4 cm to 6 cm.

The resulting volumes of necrosed tissue will generally be larger than those achievable with a single array device, such as the prior LeVeen™. Needle Electrode discussed above. The treatment volumes achievable with the present invention may be at least 30 cm³ or larger, often being 70 cm³ or larger, sometimes being 150 cm³ or larger, and typically being in the range from 50 cm³ to 70 cm³.

In other preferred embodiments of the apparatus of the present invention, the first and second electrode arrays will be electrically isolated from each other in order to permit bipolar energization, i.e., to allow each electrode array to be separately connected as individual poles to an electrosurgical, radiofrequency, or other power supply. Such embodiments will typically include separate connectors for each of the electrode arrays in order to permit bipolar connection and operation. Of course, such separately connectable electrode arrays can also be operated individually in combination with a separate dispersive electrode, either externally mounted or internally mounted, as described for example, in copending application Ser. No. 09/656,307, the full disclosure of which is incorporated herein by reference. In other embodiments, the first and second electrode arrays may be electrically coupled to permit common monopolar operation, although such monopolar operation will generally be less desirable. The first and second electrode arrays may be coupled internally, i.e., within the electrode deployment device itself, or externally, e.g., in the power supply and/or in the cable(s) connecting the electrode deployment device to the power supply.

In still other preferred embodiments, at least the first electrode array will include a first axial conductor extending proximally along the shaft from the first electrode array. The first axial conductor will be electrically coupled to the first electrode array so that they will operate at the same electrical potential. Usually, the second electrode array will also include an electrically coupled axial conductor which extends distally along the probe shaft. The first and second axial conductors will thus be opposed (as are the first and second electrode arrays). A gap will remain between the termini of the axial conductors to maintain electrical isolation between the first and second electrode arrays. Usually, the gap will be in the range from 0.5 cm to 5 cm, preferably from 1 cm to 3 cm. Typically, arrays having smaller diameters will require less spacing in order to maintain isolation, thus requiring smaller gaps. At least the first axial conductor will preferably extend axially in the proximal direction beyond the tips of the electrodes of the first array. Usually, if a second axial conductor is employed, its tip will extend axially in a distal direction beyond the tips of the electrodes of the array. Thus, in an exemplary embodiment, the tips of both axial conductors will be closer to each other than the tips of the electrodes in the respective electrode arrays.

In another aspect of the present invention, methods for treating a treatment region in tissue comprise deploying a first electrode array in tissue on one side of the treatment region. A second electrode array is deployed in tissue along an axis with the first array and on the other side of the treatment region. Both the first and second electrode arrays have concave sides and convex sides, and a concave side of the first array faces a concave side of the second array when the electrodes are fully deployed. After deploying the electrodes, an electrical current, usually a bipolar radiofrequency current, is applied from the first and second electrode arrays through the intervening tissue.

Usually, deploying the first electrode array comprises introducing a first probe through tissue to a location on one side of the treatment region and advancing a first plurality of at least three electrodes from the probe in an everting pattern. The second electrode array is deployed similarly by advancing a second plurality of at least three electrodes from the probe in an everting pattern at a location on the other side (typically opposite) of the treatment region. In the exemplary embodiments, the second electrode array is deployed from the same probe as was the first electrode array. Alternatively, the second electrode array may be deployed from a second probe through tissue to the location on the other side of the treatment region, e.g., the side opposite to the first electrode array.

The methods of the present invention are useful for treating a wide variety of tissues, particularly liver, lung, kidney, pancreas, stomach, spleen, uterus, and the like. Usually, the treatment region is a tumor or other diseased region and the treatment regions are imaged and identified using conventional techniques capable of elucidating a target tissue, such as ultrasonic scanning, magnetic resonance imaging (MRI), computer-assisted tomography (CT), fluoroscopy, nuclear scanning (using radiolabeled tumor-specific probes), and the like.

Tissue necrosis is preferably achieved by applying radiofrequency current in an amount and for a time sufficient to thermally destroy the tissue. Usually, the electrical current is applied at a frequency in the range from 300 kHz to 1.2 MHz. The current is applied at a power level selected to achieve the ablation, typically being in the range from 20 W to 300 W, usually from 50 W to 200 W. In the exemplary embodiments, the electrical current is supplied from a radiofrequency power supply in a bipolar manner where the first and second electrode arrays are attached to opposite poles of the power supply.

The methods of the present invention will preferably employ first and second electrode arrays having the dimensions set forth above with respect to the probes of the present invention and will preferably produce lesions having the volumes defined by probes, as set forth above.

Preferably, the methods will employ a first electrode array having a first axial conductor extending at least part of the way toward the second electrode array along an axis therebetween. The first axial conductor will be electrically coupled to the first electrode array and will terminate at a point located axially beyond the termination points of the electrode wires in the first electrode array, typically by a distance in the range from 5 mm to 10 mm. Such extension of the first axial conductor axially beyond the first electrode array, places the conductor closer to the second electrode array and optional second axial conductor. Thus, a preferred central electrical conduction path is provided between the first and second arrays. Usually, the second electrode array will also include a second axial conductor extending part of the way to the first array, and the second axial conductor will usually extend axially beyond the tips of the electrodes in the second electrode array. Thus, in a preferred embodiment, the proximal ends of the first axial conductors and the distal ends of the second axial conductors will lie closer to each other than will any of the tips of the individual electrodes in the two respective electrode arrays. Such a structure will provide a preferred electrical conduction path through a gap left between the termini of the first and second axial conductors. The current path and resulting current flux between the first and the second arrays is thus concentrated initially within the center of the tissue volume being treated (i.e., along the axis between the two arrays) which would not be the case in the absence of the axial conductors.

It has been further found that the use of the preferred everting electrodes in the first and second arrays defines a generally ovoid lesion volume generally bounded by an outer cylindrical wall having hemispherical ends. Use of the axial conductors along the axis between those arrays helps to assure that tissue in the center of the treatment region is treated before the tissues lying at the outer cylindrical and hemispherical peripheries of the treatment region is treated. After the central portions of the treatment region have been heated and necrosed to the extent that impedance to current flow increases, the individual electrodes of the electrode arrays will continue to heat and treat the outer portions. This two-step approach helps to assure that the entire volume, including both inner and outer portions of the treatment volume, is adequately necrosed.

Preferential heating of the center of the lesion can also reduce the effect of non-uniform blood flow at different points within the region to be treated. Destruction of the blood vessels within the center of the treatment region of tissue will tend to reduce perfusion differences in the larger, outer shell of the region. Moreover, even if the two electrode arrays experience different cooling because of such differences in blood flow, the everted configuration of the two opposed electrode arrays will enhance creation of a substantially contiguous shell surrounding the preferentially heated core. This effect further reduces the non-uniformities created by differential cooling which has been a major problem in prior efforts to treat large tissue volumes with bipolar radio frequency ablation.

In a further aspect of the present invention, methods for bipolar radiofrequency necrosis of the tissue comprise deploying a first array of electrodes and a second array of electrodes in tissue. The first electrode array is deployed on one side of a treatment region and includes both a transverse face and an axial conductor extending in an axial direction from the transverse face. Usually, the electrode array which is located distally, i.e., furthest away from the entry point, will be deployed first in order to permit unimpeded imaging of the target tissue and the electrode during deployment. For that reason, the use of devices having separately deployable electrode arrays will often be preferred. Similarly, the second electrode array includes a transverse face and an axial conductor extending in an axial direction opposed to the first axial conductor on the first electrode array. Bipolar radiofrequency current is then applied between the two electrode arrays to heat and necrose tissue therebetween. The first and second electrode arrays will preferably have concave surfaces and fully everted electrode tips which face each other, but the use of such concave electrode arrays is not necessary. For example, the electrode arrays may be radially divergent, but not actually evert. Alternatively, the electrode arrays may be deployed by using a diverter to turn straight electrodes radially outward, as generally described in German patent application 2124684 to Stadelmayr.

The transverse faces of the first and second electrode arrays are preferably introduced from a single probe, but optionally could be introduced using two separate probes, such as two separate LeVeen™. Needle Electrodes as described previously. The LeVeen™. Needle Electrodes would have to be modified to include the axial conductors, as described in more detail below.

The tissues to be treated and the treatment conditions will be generally the same as described above in connection with the earlier embodiments of the methods of the present invention. Similarly, the electrode array dimensions will generally be the same as described above, except that the electrodes need not be concave or everting in all embodiments.

The present invention still further comprises kits including one or more probes capable of deploying at least first and second electrode arrays, generally as described above. The kits will further include instructions for use for deploying the electrode arrays and applying bipolar radiofrequency current for treating a tumor or other diseased condition within a target body tissue. The method set forth in the instructions for use will generally be in accord with any of the methods described above for the present invention. Usually, the treatment probe will be packaged in a conventional medical device package, such as a tray, box, tube, pouch, or the like. The instructions for use may be provided on a separate sheet of paper or may be printed in whole or in part on a portion of the packaging.

BRIEF DESCRIPTION OF THE DRAWINGS

FIG. 2 illustrates a first exemplary electrode array deployment probe constructed in accordance with the principles of the present invention.

FIG. 3 is an enlarged portion of the electrode deployment array of FIG. 2 shown with portions broken away.

FIG. 4 illustrates the electrode deployment probe of FIG. 2, shown with the electrodes retracted.

FIG. 5 is an enlarged view of the distal end of the probe of FIG. 4

FIG. 6 illustrates a second exemplary electrode deployment probe constructed in accordance with the principles of the present invention.

FIG. 7 is a detailed view of the distal end of the probe of FIG. 6.

FIGS. 12A-12C illustrate the manner in which the electrode arrays are deployed from the probe of FIG. 10.

DESCRIPTION OF THE SPECIFIC EMBODIMENTS

Figure 1:
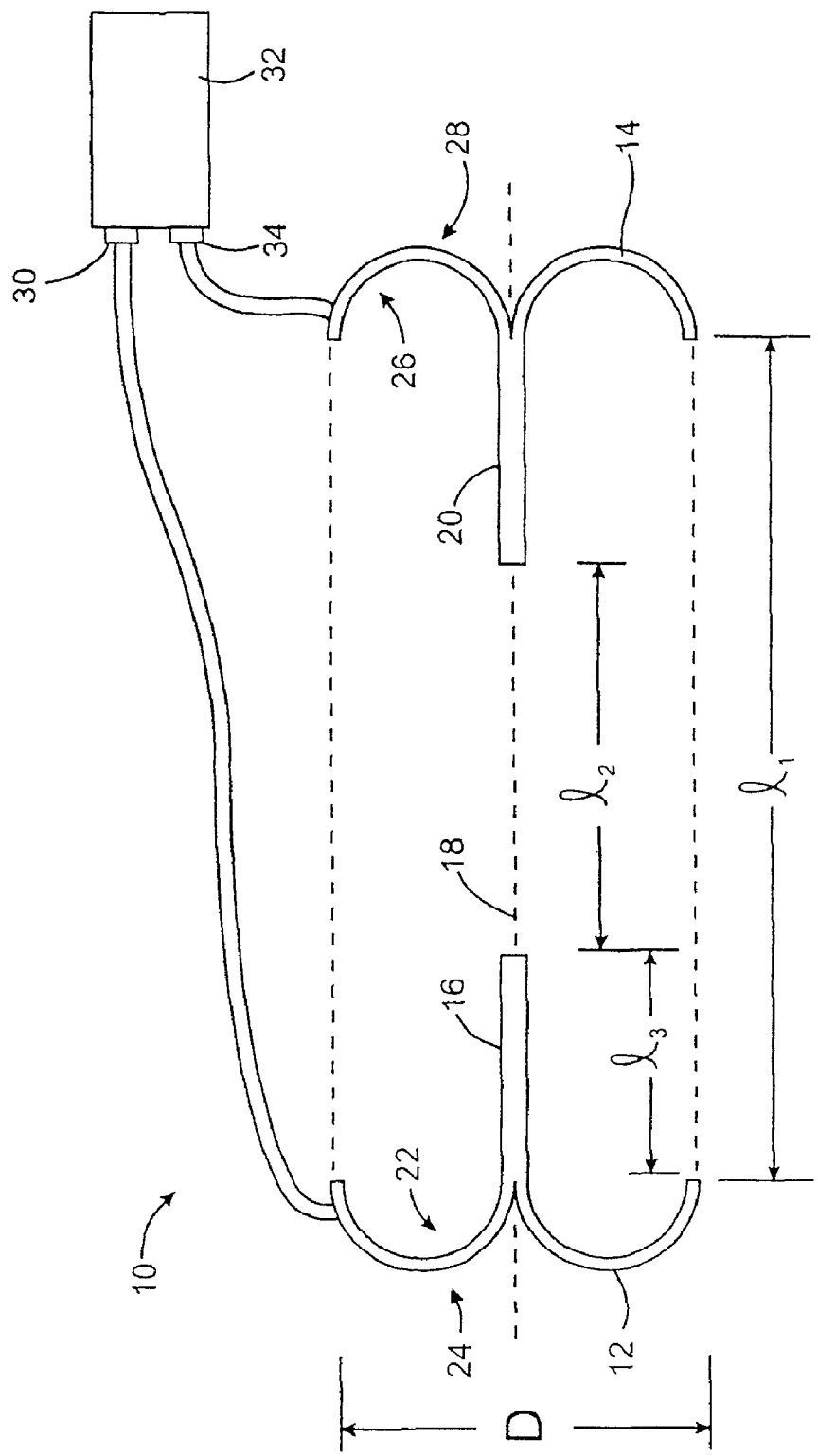
FIG. 1 is a schematic illustration of the deployment of a first electrode array and a second electrode array in accordance with the methods of the present invention

The present invention is intended to position electrode arrays, particularly bipolar arrays, relative to treatment regions within solid tissue of a patient. The treatment regions may be located anywhere in the body where hyperthermic exposure may be beneficial. Most commonly, the treatment region will comprise a solid tumor within an organ of the body, such as the liver, lung, kidney, pancreas, breast, prostate (not accessed via the urethra), uterus, and the like. The volume to be treated will depend on the size of the tumor or other lesion, but the present invention is particularly suitable for treating large treatment regions having the volumes and geometries set forth above. The peripheral dimensions of the treatment region may be regular, e.g., spherical or ellipsoidal, but will more usually be somewhat irregular. The lesion created to enclose the target tissue region utilizing this invention will usually be cylindrical or a truncated conical volume, as described in more detail below. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound which can be employed to monitor the size and location of the tumor or other target tissue being treated, either intraoperatively or externally.

Apparatus according to the present invention will usually comprise at least one probe having a distal end adapted to be positioned beneath a tissue surface at or near the treatment region or regions. A first array of electrodes comprising a plurality of tissue-penetrating electrodes, typically in the form of sharpened, small cross-section metal elements are reciprocatably attached to the probe so that they penetrate into tissue as they are advanced from a first specific site (referred to hereinafter as the first target site) at or adjacent to a peripheral boundary of the treatment region, as described in more detail hereinafter. The primary requirement of such electrode elements is that they can be deployed in an array, preferably a three-dimensional array, emanating from the first treatment site within the treatment region of the tissue. Usually, the first electrode array will be deployed from a first target site on a "distal" side of the treatment region, i.e., the side which is most remote from the organ or tissue entry point. In the exemplary embodiments, the electrode elements are first introduced to the treatment region in a radially collapsed or other constrained configuration, and thereafter advanced into the tissue from a delivery cannula or other element in a divergent pattern to achieve the desired three-dimensional array. The electrode elements will diverge radially outwardly from the delivery cannula (located at the first target site) in a uniform pattern, i.e., with the spacing between adjacent electrodes diverging in a substantially uniform and/or symmetric pattern. Preferably, adjacent electrodes will be spaced-apart from each other in similar or identical, repeated patterns and will usually be symmetrically positioned about an axis of the delivery element. The electrode elements may extend or project along generally straight lines from the probe, but will more usually be shaped to curve radially outwardly and to evert proximally so that they face partially or fully in the proximal direction when fully deployed. It will be appreciated that a wide variety of particular patterns can be provided to uniformly cover the region to be treated.

Apparatus according to the present invention will also comprise at least a second array of electrodes comprising a plurality of tissue-penetrating electrodes typically in the form of sharpened, small cross-section metal wires or elements. The second electrode array will usually be attached to the same probe as is the first electrode array. In some instances, however, the methods of the present invention may utilize first and second electrode arrays which are deployed from separate probes and operated in a bipolar manner, as described in more detail below. The electrode wires or elements of the second array will be deployed from a second target site within the treatment region, usually on a "proximal" side thereof, i.e., the side which is closest to the organ or tissue entry point. The electrodes of the second array will be introduced similarly to those of the first array, i.e., in a collapsed configuration, and subsequently deployed radially outwardly. In the exemplary embodiments, both the first and the second electrode arrays include everting electrode elements which form arrays having generally concave and convex surfaces. By facing the concave surfaces and electrode tips of the two electrode arrays toward each other so that they are generally aligned along a common axis, usually defined by a shaft of the probe, radio frequency and other high frequency currents may be applied to tissue in a manner which creates a uniform lesion, i.e., a lesion which is continuous and without significant portions of viable tissue, even when the region has portions which have different perfusion and different cooling characteristics.

Figure 1A:
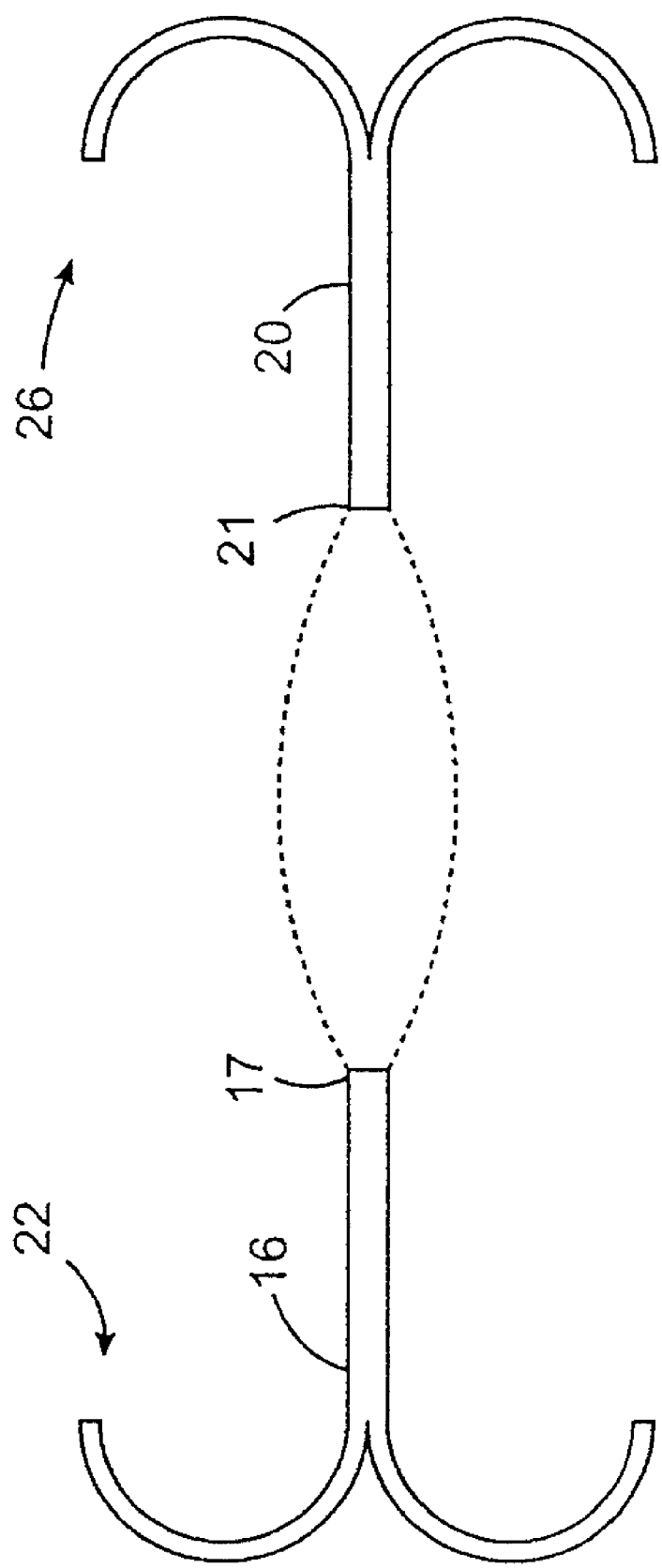
FIGS. 1A-1C are schematic illustrations of the progression of tissue ablation achieved with the preferred treatment apparatus and methods of the present invention.

Referring now to FIG. 1, a system 10 comprising a first electrode array 12 and a second electrode array 14 is schematically illustrated. The electrode arrays 12 and 14 are shown as fully everting arrays where individual electrode wires extend first in an axial direction, diverge radially outwardly, and turn back upon themselves until they face in an opposite direction from which they began. The first electrode array 12 further includes an axial conductor 16 which extends along an axis line 18 toward a second axial conductor 20 which is part of the second electrode array 14. The first electrode array 12 has a concave surface 22 and a convex surface 24, and the second electrode array 14 also has a concave surface 26 and a convex surface 28. In a preferred aspect of the present invention, the concave surfaces at 22 and 26 of the electrode arrays 12 and 14 face each other along the axis line 18. The first axial conductor 16 and the second axial conductor 20 also face each other and extend toward each other, (usually beyond the inward terminations of the metal elements of the corresponding arrays 22 and 26) leaving a gap between the distal termini of each conductor 16 and 20 which is less than the distance between the inward terminations of the arrays 22 and 26. The current flow will initially be concentrated in this gap which is located in the central core of the tissue treatment region, as illustrated in FIG. 1A above. Preferably, the distance $l_2$ between the inner termini 17 and 21 of the axial conductors 16 and 20 will be in the range from 0.25 to 0.75 of the distance $l_1$ between the inner termini of the innermost portions of the electrode arrays 24 and 26. The treatment region will thus be heated and necrosed from the center outward, thus enhancing the ability to completely and uniformly necrose the entire tissue volume of the treatment region defined by the outward perimeters of the arrays 22 and 26, as illustrated in FIG. 1C above.

In the methods of the present invention, the first electrode array 12 and the second electrode array 14 will be disposed within tissue on opposite sides of a treatment region. The arrays will be disposed generally as shown in FIG. 1, preferably with the axial conductors 16 and 20 aligned along a common axis line, most preferably being positioned on a single probe shaft, as will be described in more detail hereinafter. The first electrode array 12 is connected to a first pole 30 of a radiofrequency power supply 32. A second electrode array 14 is connected to the other pole 34 of the power supply 32. In this way, the first electrode array and second electrode array will be powered in bipolar manner in order to effect radiofrequency current flow through the tissue volume between the arrays. Tissue destruction by the current will define the treatment region.

The geometry and volume of the treatment region within the patient tissue is determined by controlling various dimensions of the apparatus. For example, the arrays 12 and 14 will usually have outer circular diameters D in the range from 1 cm to 6 cm, usually from 2 cm to 4 cm. The diameters of each array will usually be the same, although they could differ in certain circumstances. When the diameters are the same, the geometry of the lesion created will be generally cylindrical. When the diameters are different, the geometry could generally be a truncated cone. The distance between the electrode arrays $l_1$ will usually be in the range from 2 cm to 10 cm, more usually in the range from 3 cm to 7 cm, and preferably in the range from 4 cm to 6 cm. The axial conductor 16 will typically have a length in the range from 0.5 cm to 2 cm, and the gap between the distal termini of the axial conductors 16 and 20 will typically have a length 2 in the range from 0.5 cm to 5 cm, usually from 1 cm to 3 cm. Usually, the inner termination 17 of the first axial conductor 16 will extend beyond the inner terminations of the individual electrodes in a first electrode array 22 by a distance $l_3$ in the range from 0.5 cm to 2 cm, preferably from 0.7 cm to 1.3 cm. Similarly, the axial conductor 20 associated with the second electrode array 26 will terminate inwardly at 21 relative to the inward terminations of the individual electrodes, typically by a length in the ranges just set forth, more typically, having a length equal to $l_3$ as also in the first axial conductor 16. The use of the axial conductors 16 and 20 is generally preferred since they provide a preferred current return path in bipolar operation which increases the current flux within the center of the region being treated. Such increased current flux, in turn, assures that the center of the treated region, e.g., along the axis line 18 between the tips 17 and 21 of the axial conductors 16 and 20, will be preferentially heated prior to the heating and necrosis of the outer portions of the treatment region. If the outer portions of the treatment region were treated first, it might be more difficult to assure that all portions, and in particular the inner portions, of the treatment region are adequately treated.

Figure 1B:
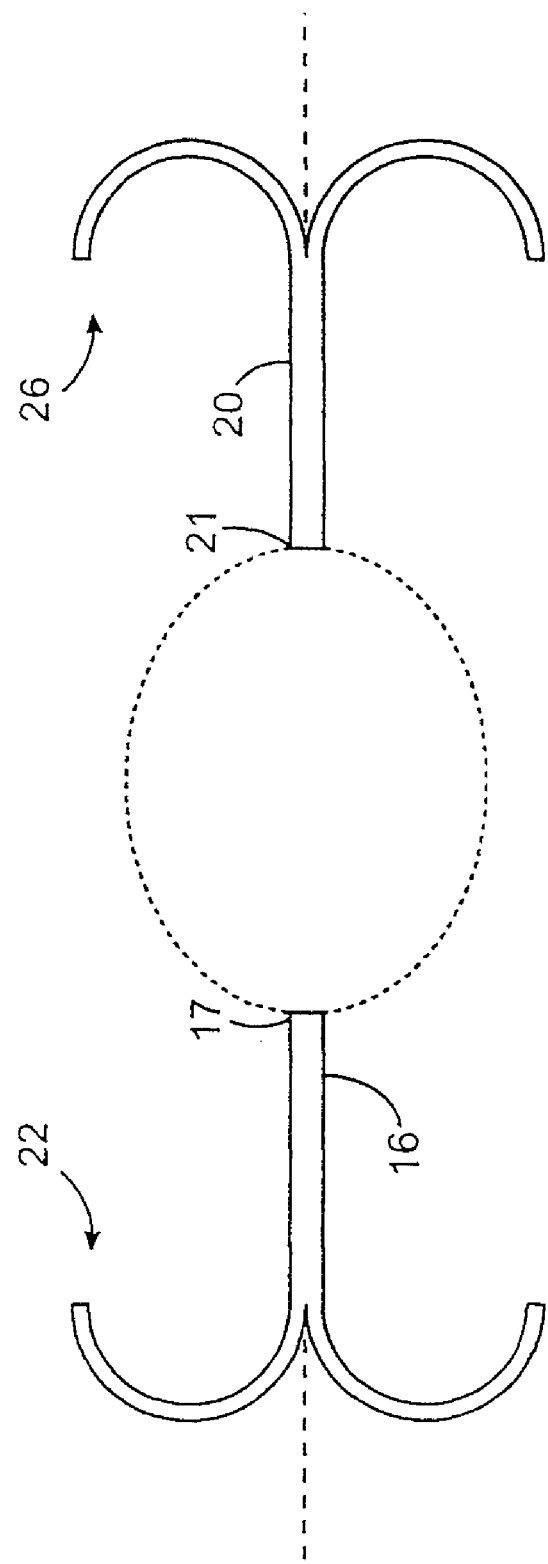
Figure 1C:
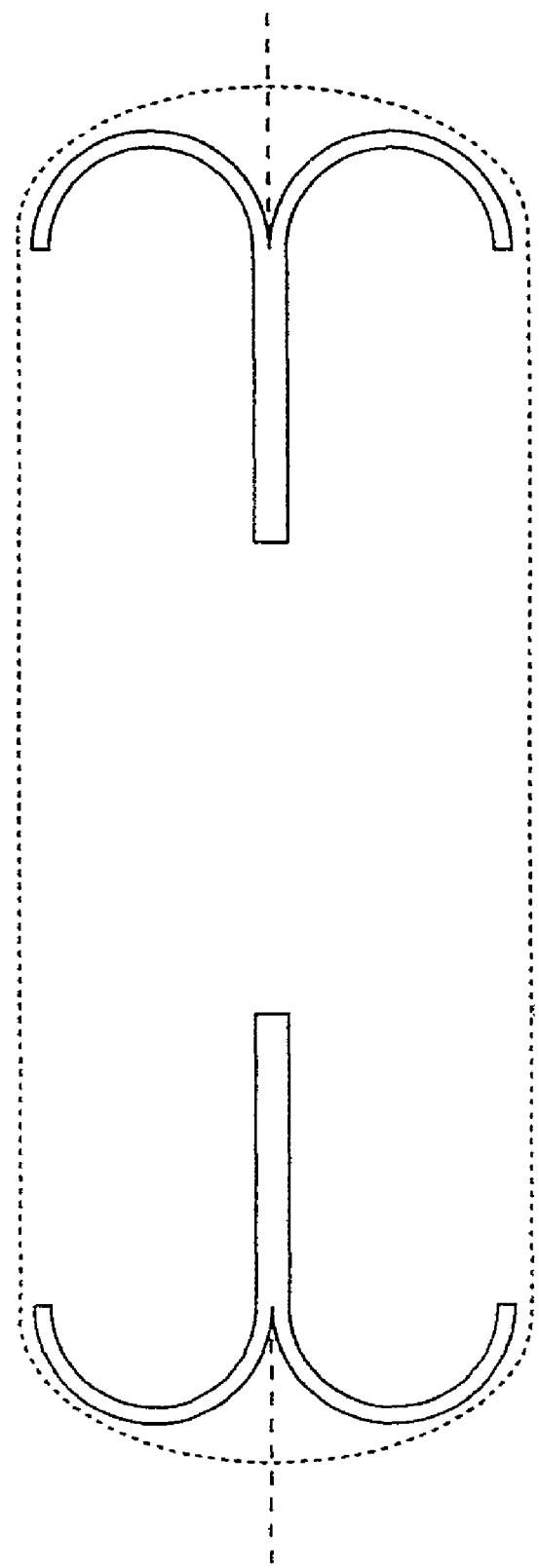

Referring to FIGS. 1A-1C, the propagation of the tissue necrosis region achieved by the apparatus and methods of the present invention is schematically illustrated. Initially, the current flux is concentrated between the tips 17 and 21 of the axial conductors 16 and 20, resulting in a relatively small generally cylindrical or ovoid necrosis region, as shown in FIG. 1A. As the tissue become necrosed, its impedance increases, causing the current flux to move outwardly beyond the central core, creating a spheroidal region of necrosis, as shown in FIG. 1B. After the central region between arrays 22 and 26 including most or all of the volume surrounding the axial conductors becomes more fully necrosed, and the impedance increases over an even larger volume, current flow between the inner most tips of the individual conductors of the arrays 24 and 26 will increase, eventually resulting in the entire region between the arrays becoming necrosed, as shown in FIG. 1C. Usually, the region of necrosis will extend slightly beyond the arrays themselves due to heat conduction from the tissue which is being directly heated by the electrical current flow. In addition to the impedance increase, the reduction of blood flow through the central portions of the treatment region as that tissue becomes necrosed will also contribute to the uniformity of heating and subsequent necrosis of the larger volume. That is, as the blood flow through the treatment region is decreased, the ability to uniformly heat the tissue via the passage of current is enhanced.

The RF power supply 32 may be a conventional general purpose electrosurgical power supply operating at a frequency in the range from 300 kHz to 1.2 MHz, with a conventional sinusoidal or non-sinusoidal wave form. Such power supplies are available from many commercial suppliers, such as Valleylab, Aspen, and Bovie. Most general purpose electrosurgical power supplies, however, are constant current, variable voltage devices and operate at higher voltages and powers than would normally be necessary or suitable for the methods of the present invention. Thus, such power supplies will usually be operated initially at the lower ends of their voltage and power capabilities, with voltage then being increased as necessary to maintain current flow. More suitable power supplies will be capable of supplying an ablation current at a relatively low fixed voltage, typically below 200V (peak-to-peak). Such low voltage operation permits use of a power supply that will significantly and passively reduce output in response to impedance changes in the target tissue. The output will usually be from 50 W to 200 W, usually having a sinusoidal wave form, but other wave forms would also be acceptable. Power supplies capable of operating within these ranges are available from commercial vendors, such as Radionics and RadioTherapeutics Corporation. A preferred power supply is model RF-2000, available from RadioTherapeutics Corporation, Mountain View, Calif., assignee of the present application.

The probe which contains the deployable electrode element arrays will usually comprise an elongate shaft, typically a rigid or semi-rigid, metal or plastic cannula. In some cases, the cannula will have a sharpened tip, e.g., be in the form of a needle, to facilitate introduction to the tissue treatment region. In such cases, it is desirable that the cannula or needle be sufficiently rigid, i.e., have sufficient column strength, so that it can be accurately advanced through tissue. In other cases, the cannula may be introduced using an internal stylet which is subsequently exchanged for one or more of the electrode arrays. In the latter case, the cannula can be relatively flexible since the initial column strength will be provided by the stylet. The cannula serves to constrain the individual electrode elements of the electrode arrays in a radially collapsed configuration to facilitate their introduction to the tissue treatment region. The first electrode array can then be deployed to its desired configuration, usually a three-dimensional configuration, by extending distal ends of the electrode elements from the distal end of the cannula into the tissue. In the preferred case of the tubular cannula, this can be accomplished simply by advancing the distal ends of the electrode elements of the first electrode array distally from the tube so that they emerge and deflect (usually as a result of their own spring or shape memory) in a radially outward pattern. The electrode arrays of the second electrode array may then be proximally advanced from the tube so that they emerge and deflect (again, usually as a result of their own spring or shape memory) in a radially outward pattern which is a mirror image of the pattern formed by the first electrode array. Particular devices employing a single probe or elongate member for deploying such spaced-apart arrays will be described in more detail below.

Referring now to FIGS. 2-5, a first exemplary electrode probe 50 will be described. The probe 50 has a coaxial design with a distal electrode array 52 and a proximal electrode array 54. The distal electrode array 52 is deployed by a distal conductor 56 which is attached to a slider 58 having a threaded end 60. The proximal electrode array 54 is attached to a proximal conductor 62 which, in turn, is attached to a proximal yoke 64. The proximal yoke 64 also has a threaded end 66 in a handle 68 of the probe 50. The handle 68, in turn, includes a stationary portion 70 and a rotatable portion 72. The rotatable portion 72 has a first threaded channel 74 which receives the threaded end 60 of the distal array slider 58. A second threaded channel 76 receives the threaded end 66 of the proximal yoke 64. In this way, rotation of the rotatable part 72 of handle 68 will simultaneously advance the distal slider 58 to deploy the distal electrode array 52 and retract the proximal yoke 64 which will deploy the proximal array 54, as best illustrated in FIG. 3. The proximal conductor 62 extends distally through an insulated outer sheath 80 and past a gap 82 (FIG. 4) between the sheath 80 and a proximal conductor tube 84. When the proximal array 50 is distally advanced, as shown in FIGS. 4 and 5, the proximal array will be contained within a central lumen of the proximal conductor tube 84. As the array 54 is proximally advanced, by rotation of handle portion 72, the individual electrode tines advanced radially outwardly through the gap 82 and eventually extend to their fully everted configuration, as shown in FIGS. 2 and 3.

While the proximal array 54 is being proximally deployed, the distal array 52 is simultaneously being deployed by advancing distally outwardly from a distal conductor tube 86 at the distal end of the probe 50. When fully deployed, a distal electrode array 52, as shown in FIGS. 2 and 3, is in electrical contact with the distal conductor 86 so that the array and conductor form an integrated electrode array of the type illustrated in FIG. 1. Similarly, the proximal electrode array 54 is in electrical contact with the proximal conductor tube 84. The two arrays and respective conductors form an integrated electrode structure similar to that shown in FIG. 1. A non-conductive gap 88 remains between the conductor tubes 86 and 84.

The probe 50 may be employed by introducing the probe into target tissue with both electrode arrays 52 and 54 completely withdrawn within their respective conductors 84 and 86. The probe 50 may be introduced directly using the sharpened distal tip 90 formed at the distal end of the distal conductor 84. Once at the desired target site, which may be determined using various imaging techniques as described above, the rotating portion 72 of handle 68 is rotated in order to advance both electrode arrays 52 and 54 into tissue. Thus, the two electrode arrays together envelope a tissue volume which becomes the treatment region when electrical power is applied. The proximal conductor 62 and distal conductor 56 are then connected to an electrosurgical power supply through connectors (not shown) on the handle 68.

Referring now to FIGS. 6 and 7, a second exemplary probe 100 constructed in accordance with the principles of the present invention will be described. The probe 100 includes a distal array 102 and a proximal array 104, each of which comprise a plurality of individual everting electrodes which may be similar in construction to those described in connection with probe 50. The distal array 102 is connected through a conductor 106 to a first rack 108. The proximal array 104 is connected to a conductor 110 which is connected to a second rack 112. The racks 108 and 112 are coupled by a pinion gear 114 so that pulling on a knob 116 in a proximal direction (arrow 118) causes the first rack 108 to move proximally and the second rack 112 to move distally. This way, the distal array 102 which is connected to rack 108 will be retracted proximally within the probe while the proximal array 104 will be retracted distally within the probe. Unlike probe 50, however, the distal array 102 and proximal array 104 are disposed in different, parallel tubular structures. The distal array 102 is disposed in a distal conductor tube 120, as best shown in FIG. 7, and the proximal array 104 is disposed in a proximal conductor tube 122. The distal conductor tube 120 and proximal conductor tube 122 are both electrically conductive so they act as axial conductors in conjunction with their respective arrays. Moreover, an insulated gap 124 exists between the electrically conductive tubes 120 and 122 to provide a gap between them, as generally described previously. Additionally, the distal tip 126 of at least the distal conductor tube 120 will be sharpened to facilitate tissue insertion. Optionally, the insulated gap region 124 at the distal end of the proximal conductor 122 may also be tapered or beveled in order to facilitate insertion.

As best seen in FIG. 7, the proximal conductor 110 and distal conductor 106 will both extend through parallel tubes which are covered by an insulating material 130. Thus, the probe 100 may be used in generally the same manner as described for prior probe 50.

Figure 8:
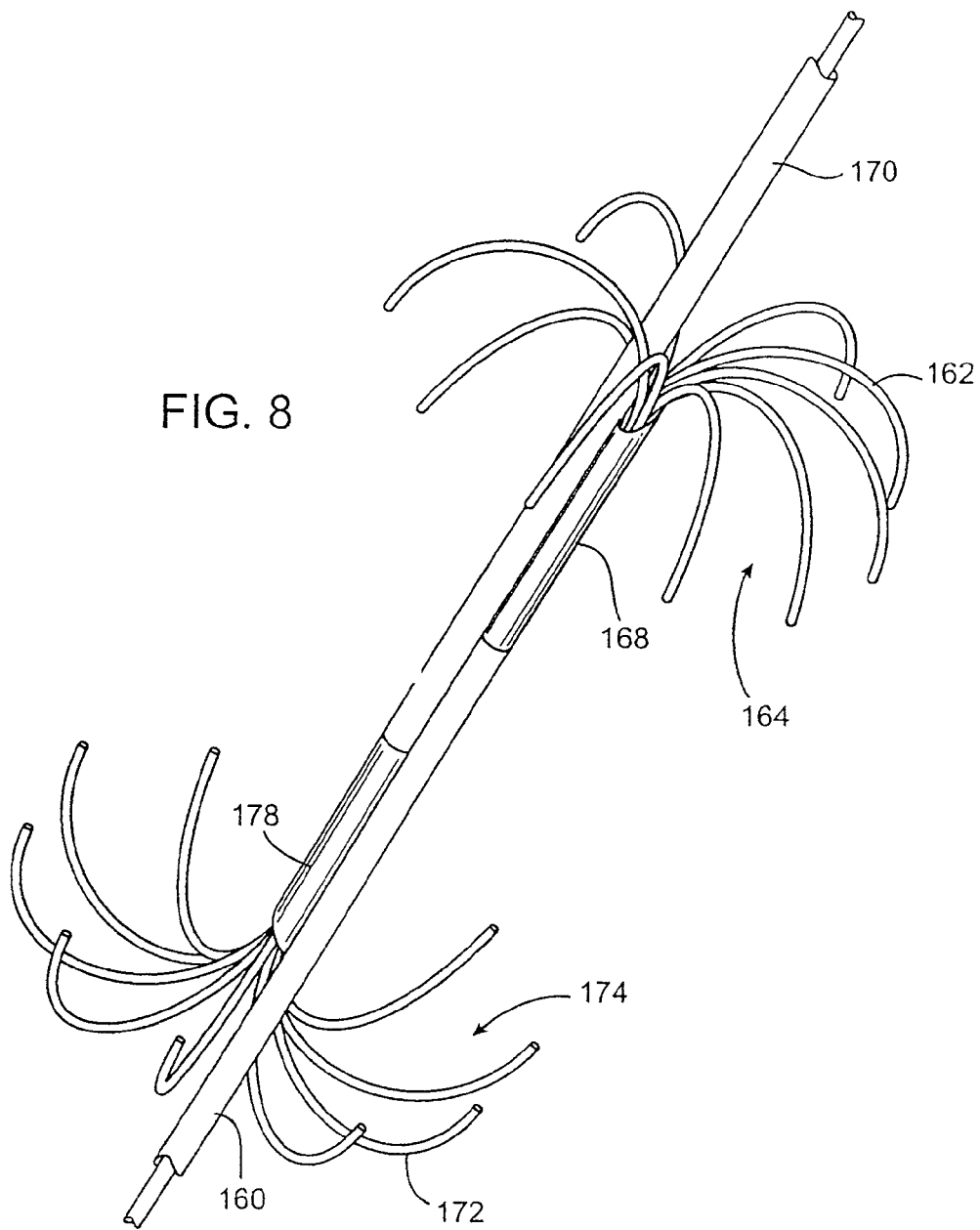
FIG. 8 illustrates the use of a pair of separate electrode deployment probes for deploying electrodes in accordance with the methods of the present invention/

Referring now to FIG. 8, the methods of the present invention may be performed using separate electrode deployment probes 160 and 170, such as the LeVeen™ Needle Electrodes described previously. To use such separate probes, they should be inserted to a tissue region in generally opposite directions along coincident axes to lie side-by-side, as illustrated in FIG. 8. The electrode arrays 162 and 172 may then be deployed in a manner such that the concave faces 164 and 174 of the arrays are opposed along a generally axial line therebetween. Preferably, at least a portion of each probe 160 and 170 will be modified to provide an axial conductor. For example, a distal portion 168 of the shaft of electrode deployment probe 160 may have an insulating sheath removed so that it becomes electrically conductive. In this way, the deployed array 162 will be electrically coupled to a conductor region 168 which forms an axial conductor for use in the methods of the present invention. Similarly, a distal portion 178 of probe 170 may also have its insulation removed so that it becomes electrically active and acts as an axial conductor in combination with the electrode array 172. Once the electrode arrays 162 and 172 are deployed as shown in FIG. 8, they may be electrically powered and used to perform methods according to the present invention as described above.

Figure 9:
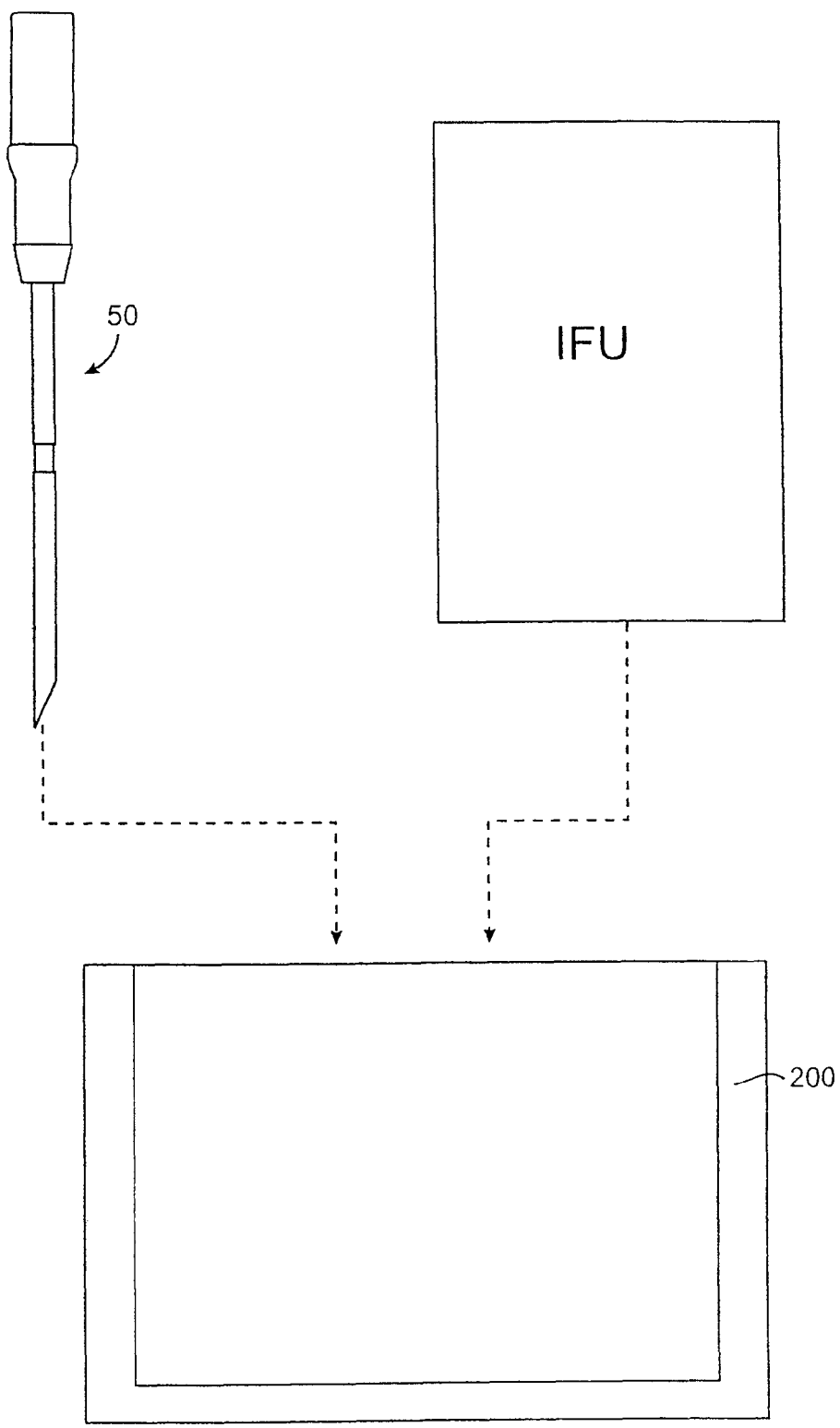
FIG. 9 illustrates a kit including an electrode deployment probe, instructions for use, and packaging in accordance with the principles of the present invention.

Referring now to FIG. 9, a kit according to the present invention will include at least a single electrode deployment probe, such as probe 50, and instructions for use IFU. The instructions for use will set forth a method for deploying a pair of electrodes from probe 50 in tissue in accordance with any of the methods described hereinabove. The instructions for use will generally be written on a package insert or other separate piece of paper or enclosure, but could also be printed in whole or in part on other packing materials. Usually, all components of the kit will be packaged together in a conventional package 200, such as a pouch, tray, box, tube, or the like. Preferably, the probe 50 will be sterilized within the package so that they are immediately ready for use in a sterile environment.

Figure 10:
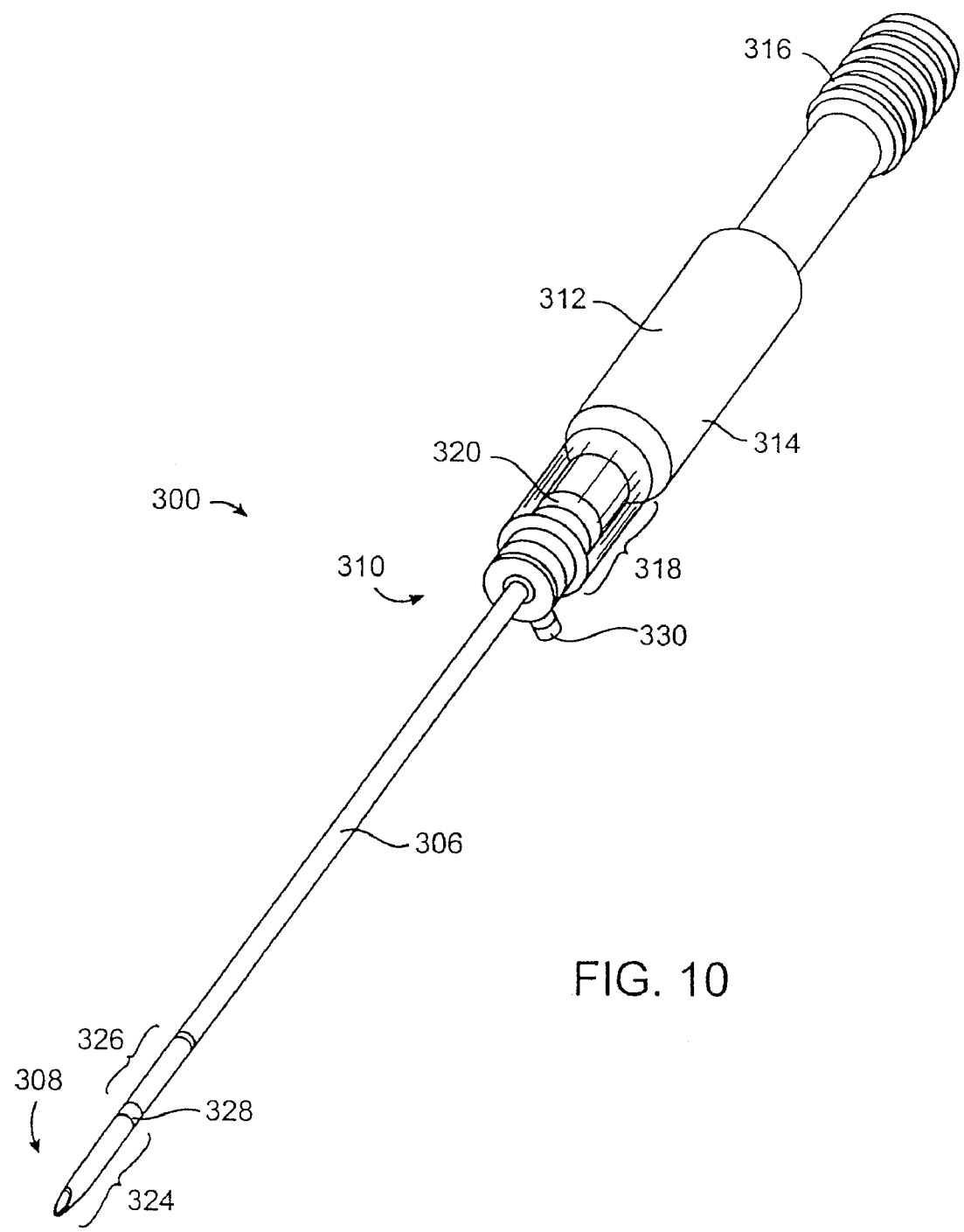
FIG. 10 is a perspective view of a third exemplary electrode deployment probe constructed in accordance with the principles of the present invention.
Figure 11A:
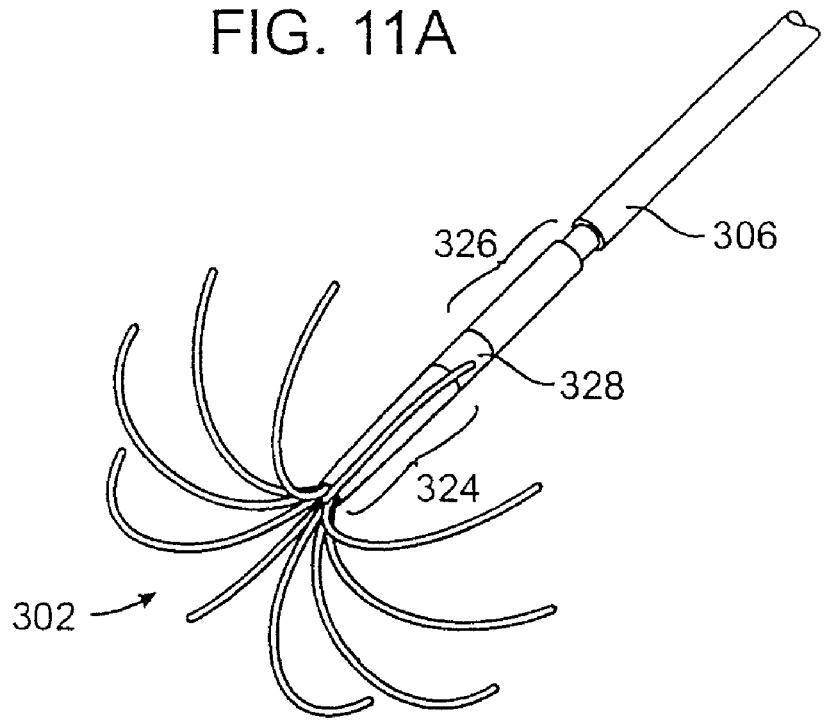
FIGS. 11A and 11B are detailed views of the distal end of the probe of FIG. 10 illustrating a distal array deployed (FIG. 11A) and distal and proximal probes deployed (FIG. 11B).
Figure 11B:
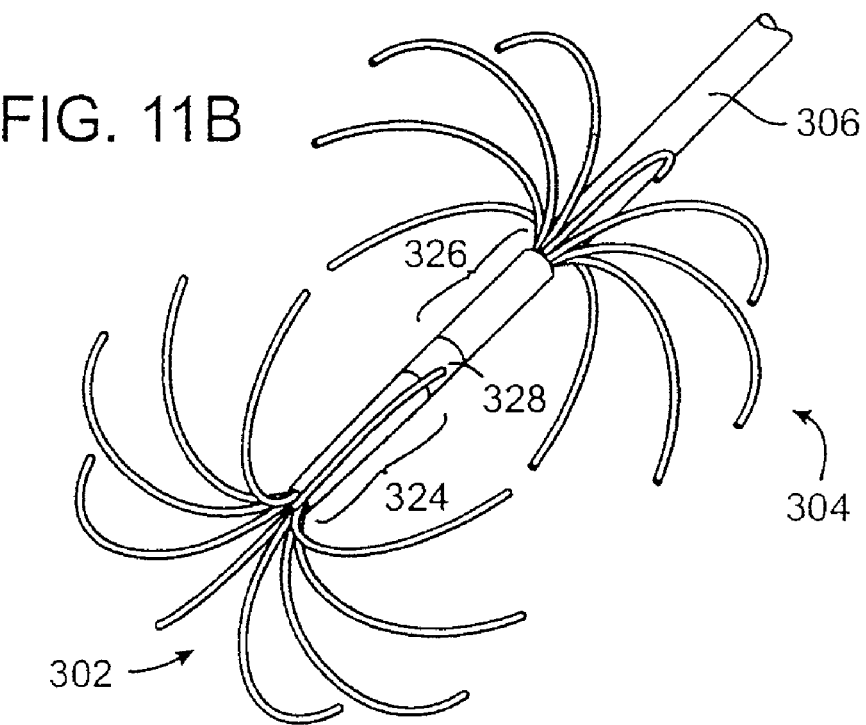

Referring to FIGS. 10, 11A, and 11B, a fourth exemplary electrode probe 300 will be described. The electrode probe 300 has a coaxial design with a distal electrode array 302 (FIG. 11A) and a proximal electrode array 304 which may be separately deployed. As shown in FIG. 11A, the distal electrode array 302 has been deployed while the proximal array 304 remains retracted within the electrode probe 300. As shown in FIG. 11B, both the distal electrode array 302 and the proximal electrode array 304 have been deployed. While it is not illustrated, it also possible to deploy the proximal electrode array 304 without having deployed the distal electrode array 302.

The primary components of the electrode probe 300 are generally the same as those for the prior embodiments of the electrode probes of the present invention. The electrode probe 300 includes a shaft 306 having a distal end 308 and a proximal end 310. A handle structure 312 is attached to the proximal end 310 of the shaft 306 and includes a cylindrical body 314 and a deployment knob 316. A portion or region 318 of the cylindrical body 314 is transparent to permit viewing of a translatable marker ring 320, as will be described in more detail hereinafter. The shaft 306 will preferably have a sharpened or otherwise tissue-penetrating tip 322, as generally described above in connection with prior embodiments.

The distal array 302 will be electrically coupled to a portion of the shaft 324, which provides the axial conductor described in connection with prior embodiments. Similarly, the proximal electrode array 304 will be electrically coupled to a second portion 326 of the shaft, which also provides an axial conductor as described above. Thus, when fully deployed, the electrode arrays 302 and 304 together with respective axial conductors 324 and 326 will provide the electrode array configuration as shown in FIG. 1. The axial conductors 324 and 326 will be separated by an electrically non-conductive portion 328 of the shaft. The electrode probe 300 will further include a first cylindrical conductor 330 for attaching an external power supply to the proximal array 304. A second conductor 332 (FIG. 13) is provided in the knob 316 of the handle structure 312 for connecting the distal array 302 to the external power supply.

Referring now to FIGS. 12A-12C, sequential deployment of the electrode arrays 302 and 304 using the electrode probe 300 will be described. As shown in FIG. 12A, the electrode probe 300 is in its initial or shelf configuration with both electrode arrays 302 and 304 being retracted within the shaft 306. The deployment knob 316 will be positioned in its proximal-most position relative to the cylindrical body 314 of handle 312. Initially after the sharpened tip 322 of shaft 306 is introduced through solid tissue to a desired target site, either the distal array 302 or the proximal array 304 may be selectively deployed. As shown in FIG. 12B, the distal array 302 is deployed by depressing the knob 326, i.e., axially translating the knob relative to the cylindrical body 312 in a distal direction so that the electrode array 302 is advanced distally from the distal end of the shaft 306. As with the prior embodiments, the distal electrode array 302 will first emerge in a distal direction and then diverge, typically to form an everted configuration as illustrated. The proximal array 306 is separately deployed by rotating the handle 316 as illustrated by the arrow 340 in FIG. 12C. Such rotation causes the proximal electrode array 304 to first advance proximally relative to the shaft 306 and then to diverge radially outwardly. Again, in the preferred embodiment, the proximal array will also evert so that its tips end up pointed toward the tips of the electrodes in the distal electrode array 302, as shown in FIG. 12C. In addition to deploying the proximal array 304, twisting of the handle 306 causes the marker ring 320 to axially translate in a proximal direction from the initial position, as shown in FIGS. 12A and 12B, to a final position as shown in FIG. 12C. Movement of the marker 320 allows the physician to visually confirm whether or not the proximal electrode array 304 has been deployed. Determination of whether the distal electrode array 302 has been deployed can readily be made based on the axial position of the knob 316. When in the proximally extended configuration of FIG. 12A, the physician knows that the distal electrode array 302 has not been deployed. When it is fully advanced in a distal direction, as shown in FIGS. 12B and 12C, the physician will know that the distal array 302 has been deployed.

Figure 13:
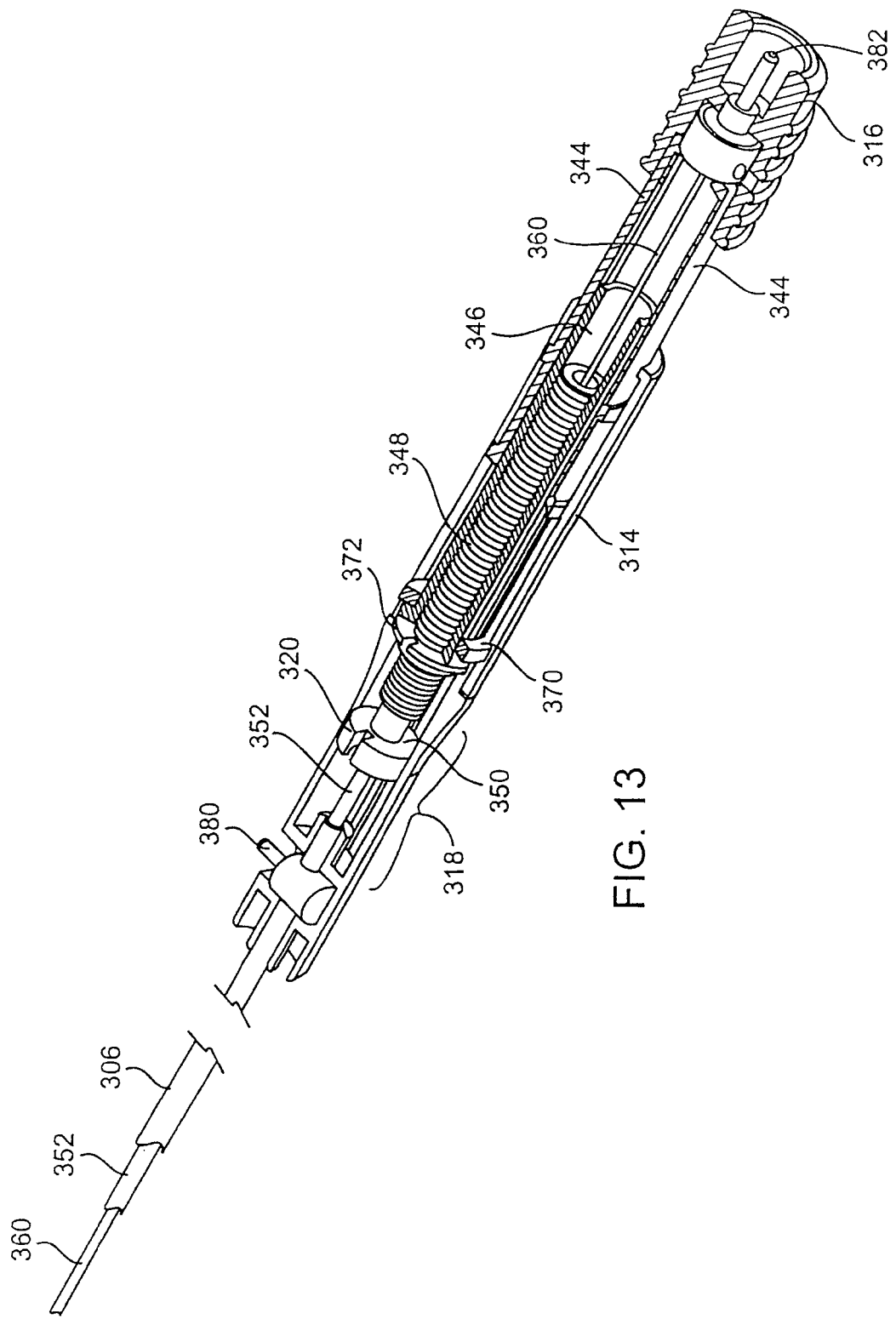
FIG. 13 is a detailed view of the handle of the probe of FIG. 10, with portions broken away.

A wide variety of internal mechanisms can be provide for allowing the separate deployment of the distal electrode array 302 and the proximal electrode array 304. A particular exemplary structure is shown in FIG. 13, where portions of the handle structure 312 are broken away to reveal the inner components thereof. The deployment knob 316 is attached to a slideable sleeve 344 which enables the knob to rotate and axially reciprocate within the body 314 of the handle, as shown in FIGS. 12A-12C above. In addition, the knob 316 captures rotatable terminal 344 which, in turn, is connected to a coupling shaft 360. Axial movement of the knob 316 causes both the terminal 342 and shaft 360 to reciprocate and deploy the distal array 302. Temporary retaining ring 370 and spacer 372 will be removed prior to deployment.

The knob 316 is also coupled to a rotatable core 346 which rotates with the knob. Rotation of the core 346 engages threads 348 on a shuttle 350 which axially translates in response to rotation of the knob 316. Axial translation of the shuttle, in turn, translates a shaft 352 which is connected to and deploys the proximal electrode array 304. In this way, the arrays 302 and 304 may be independently and separately deployed using the knob, as generally shown above in FIGS. 12A and 12C. A marker surface 320 will be present on the shuttle 350 so that the marker will move and be visible through the transparent region 318 of the handle. Electrical terminals 380 and 382 are provided for connection to a bipolar power supply, generally as shown in FIG. 1.

While the above is a complete description of the preferred embodiments of the invention, various alternatives, modifications, and equivalents may be used. Therefore, the above description should not be taken as limiting the scope of the invention which is defined by the appended claims.

The invention claimed is:

1. A tissue ablation instrument, comprising:
a probe shaft having a distal end and a proximal end;
a handle coupled to a proximal end of the probe shaft;
a first circumferentially spaced array of tissue penetrating electrodes mounted on the shaft and configured to be selectively deployed from a retracted configuration, in which the first array of electrodes are disposed within the shaft, to a deployed configuration, in which the first array of electrodes extend radially from the probe shaft to form an everting array of electrodes spaced circumferentially about a first location on the probe shaft; and
a second circumferentially spaced array of tissue penetrating electrodes mounted on the shaft and configured to be selectively deployed from a retracted configuration, in which the second array of electrodes are disposed within the shaft, to a deployed configuration, in which the second array of wire electrodes extend radially from the probe shaft to form an everting array of electrodes spaced circumferentially about a second location on the probe shaft spaced-apart proximally from the first location; and
an electrode deployment assembly housed in the handle and coupled to the respective probe shaft and first and second electrode arrays, wherein the electrode deployment assembly is configured to simultaneously deploy the respective first and second electrode arrays from their retracted configurations to their deployed configurations,
wherein, in their respective deployed configurations, the first and second electrode arrays define a volumetric tissue ablation zone.

2. The tissue ablation instrument of claim 1, wherein the first and second electrode arrays each comprise a plurality of individual electrodes which initially move axially and then evert as they are deployed.

3. The tissue ablation instrument of claim 1, wherein the probe shaft has a tissue-penetrating distal tip.

4. The tissue ablation instrument of claim 1, wherein the probe shaft has at least one cavity for receiving the first electrode array when in its retracted configuration, and at least a second cavity for receiving the second electrode array, when in its retracted configuration.

5. The tissue ablation instrument of claim 1, wherein the first electrode array defines a proximal facing concave face in its deployed configuration, and the second electrode array defines a distal facing concave face in its deployed configuration, and wherein the concave face of the first array of electrodes faces the concave face of the second array of electrodes.

6. The tissue ablation instrument of claim 1, the deployment assembly comprising
a first rack mechanically coupled the first array of electrodes, a second rack mechanically coupled the second array of electrodes, and a pinion gear interfacing with the first rack and the second rack.

7. The tissue ablation instrument of claim 6, further comprising a knob connected to the first rack, wherein the knob is movably coupled to the handle, and wherein proximal movement of the knob relative to the handle simultaneously deploys the respective first and second electrode arrays from their retracted configurations to their deployed configurations.

8. The tissue ablation instrument of claim 6, further comprising a first connector coupled to the first rack for connecting the first array of electrodes to one pole of a power supply and a second connector coupled to the second rack for connecting the second array of electrodes to another pole of the power supply.

9. The tissue ablation instrument of claim 1, wherein the first array of electrodes and the second array of electrodes each comprise at least three electrodes.

10. A tissue ablation instrument, comprising:
a probe shaft having a distal end and a proximal end;
a handle coupled to a proximal end of the probe shaft;
a first circumferentially spaced array of tissue penetrating electrodes mounted on the shaft and configured to be selectively deployed from a retracted configuration, in which the first array of electrodes are disposed within the shaft, to a deployed configuration, in which the first array of electrodes extend radially from the probe shaft to form an everting array of electrodes spaced circumferentially about a first location on the probe shaft; and
a second circumferentially spaced array of tissue penetrating electrodes mounted on the shaft and configured to be selectively deployed from a retracted configuration, in which the second array of electrodes are disposed within the shaft, to a deployed configuration, in which the second array of wire electrodes extend radially from the probe shaft to form an everting array of electrodes spaced circumferentially about a second location on the probe shaft spaced-apart proximally from the first location;
an electrode deployment assembly housed in the handle, including a first rack mechanically coupled the first array of electrodes, a second rack mechanically coupled the second array of electrodes, and a pinion gear interfacing with the first rack and the second rack and coupled to the respective probe shaft and first and second electrode arrays; and
a knob connected to the first rack, wherein the knob is movably coupled to the handle, and wherein proximal movement of the knob relative to the handle simultaneously deploys the respective first and second electrode arrays from their retracted configurations to their deployed configurations,
wherein, in their respective deployed configurations, the first and second electrode arrays define a volumetric tissue ablation zone.

11. The tissue ablation instrument of claim 10, wherein the first and second electrode arrays each comprise at least three individual electrodes which initially move axially and then evert as they are deployed.

12. The tissue ablation instrument of claim 10, wherein the probe shaft has a tissue-penetrating distal tip.

13. The tissue ablation instrument of claim 10, wherein the first electrode array defines a proximal facing concave face in its deployed configuration, and the second electrode array defines a distal facing concave face in its deployed configuration, and wherein the concave face of the first array of electrodes faces the concave face of the second array of electrodes.

14. The tissue ablation instrument of claim 10, further comprising a first connector coupled to the first rack for connecting the first array of electrodes to one pole of a power supply and a second connector coupled to the second rack for connecting the second array of electrodes to another pole of the power supply.

15. A method for treating a treatment region in tissue, comprising:
advancing a self-penetrating probe shaft into solid body tissue so as to position a distal portion of the shaft in the treatment region, the probe shaft having a handle coupled to a proximal end thereof;
proximally retracting a knob relative to the handle to simultaneously deploy a first array of electrodes from the probe shaft on one side of the treatment region, and a second array of electrodes from the probe shaft on an opposing side of the treatment region; and
applying electrical energy between the deployed first array of electrodes and the second array of electrodes to necrose the tissue region there between.

16. The method of claim 15, wherein the first electrode array defines a proximal facing concave face in its deployed configuration, and the second electrode array defines a distal facing concave face in its deployed configuration, and wherein the concave face of the first array of electrodes faces the concave face of the second array of electrodes.

17. The method of claim 15, wherein the first array of electrodes and the second array of electrodes each comprise at least three electrodes, wherein the at least three electrodes deploy in an everting pattern.

18. The method of claim 15, wherein the first array of electrodes and the second array of electrodes are separated by at least 2 cm.

19. The method of claim 15, wherein the first array of electrodes and the second array of electrodes each span a planar area in the range between 3 $cm^2$ to 20 $cm^2$ when deployed.

20. The method of claim 15, wherein the solid body tissue is selected from the group consisting of liver, lung, kidney, pancreas, stomach, uterus, and spleen.

* * * * *